US010683488B2

(12) United States Patent
Cheung

(10) Patent No.: US 10,683,488 B2
(45) Date of Patent: Jun. 16, 2020

(54) SYSTEM AND METHOD FOR CREATING CRYSTALS OF INSECT ACETYLCHOLINESTERASE

(71) Applicant: New York Structural Biology Center, New York, NY (US)

(72) Inventor: Jonah Cheung, Brooklyn, NY (US)

(73) Assignee: New York Structural Biology Center, New York, NY (US)

( * ) Notice: Subject to any disclaimer, the term of this patent is extended or adjusted under 35 U.S.C. 154(b) by 0 days.

(21) Appl. No.: 16/017,503

(22) Filed: Jun. 25, 2018

(65) Prior Publication Data

US 2018/0371437 A1 Dec. 27, 2018

Related U.S. Application Data

(60) Provisional application No. 62/524,728, filed on Jun. 26, 2017.

(51) Int. Cl.

*C12N 9/18* (2006.01)
*C07K 7/06* (2006.01)
*A01N 63/10* (2020.01)

(52) U.S. Cl.

CPC ............... *C12N 9/18* (2013.01); *A01N 63/10* (2020.01); *C07K 7/06* (2013.01); *C12Y 301/01007* (2013.01); *C07K 2319/21* (2013.01); *C07K 2319/35* (2013.01); *C07K 2319/50* (2013.01)

(58) Field of Classification Search

None

See application file for complete search history.

(56) References Cited

PUBLICATIONS

Li et al., "Crystal structure of acetylcholinesterase catalytic subunits of the malaria vector *Anopheles gambiae*", Insect Science, 2018 (epub—May 8, 2017), vol. 25, No. 4, pp. 721-724. doi:10.1111/1744-7917.12450.*

Dvir et al., "Acetylcholinesterase: From 3D Structure to Function", 187 Chemico-Biological Interactions, pp. 10-22 (2010).

Wiencek, "New Strategies for Protein Crystal Growth", 01 Annu. Rev. Biomed. Eng., pp. 505-534 (1999).

Mallender et al., "Organophosphorylation of Acetylcholinesterase in the Presence of Peripheral Site Ligands", 274 J. Biol. Chem., pp. 8491-8499 (1999).

Kronman et al. "Prod. & Secr. High Levels of Recombinant Human Acetylcholinesterase in Cultured Cell Lines:Microheterogeneity of the Catalytic Subunit",121(2)Gene 295-304 (1992).

Kuhn et al., "The Baculovirus Expression Vector pBSV-8His Directs Secretion of Histidine-Tagged Proteins", 162 Gene pp. 225-229 (1995).

Hyvonen, "Guide to Expression Construct Cloning", http://camelot.bioc.cam.ac.uk/~marko/methods/cloning.pdf (2004).

Nemetz et al., "RTS:Rapid Protein Expression Directly from PCR Fragment", Biochemica No. 2, www.Roche-Applied-Science.com (2002).

Cheung et al., "Supporting Information" for "Structures of human acetylcholinesterase in complex with pharmacologically important ligands", 7 pages, 2012, obtained from pubs.acs.org/doi/suppl/10.1021/jm300871x.

PcDNA™ 3.3-TOPO® TA Cloning Kit User Guide, May 2011.

GenBankAccession No. BC105062, Jun. 2006, 2 pages.

* cited by examiner

*Primary Examiner* — Suzanne M Noakes

(74) *Attorney, Agent, or Firm* — LaMorte & Associates, P.C.

(57) ABSTRACT

A method of creating crystals of insect acetylcholinesterase. A polynucleotide is obtained that encodes for acetylcholinesterase in a targeted insect. The polynucleotide contains a catalytic core sequence. A recombinant DNA construct is formed by adding a fusion protein and a polyhistidine tag to the catalytic core sequence. The recombinant DNA construct can be further modified by adding known mutations for resistance to insecticides. A growth medium is transfected with the recombinant DNA construct. A polypeptide encoded by the recombinant DNA construct is separated from the growth medium to form a concentrate. The polyhistidine tag is removed from the concentrate. The concentrate is exchanged into a buffer to create a buffered concentrate. Crystals, suitable for X-ray crystallography are then grown with the buffered concentrate.

16 Claims, 5 Drawing Sheets

Specification includes a Sequence Listing.

SEQ ID No. 1

AChE Anopheles gambiae

| Base No. | cDNA |
|---|---|
| 1-60 | GACGCGAACGACAACGATCCGCTGGTGGTCAACACGGATAAGGGGCGCATCCGCGGCATT |
| 61-120 | ACGGTCGATGCGCCCAGCGGCAAGAAGGTGGACGTGTGGCTCGGCATTCCCTACGCCCAG |
| 121-180 | CCGCCGGTCGGGCCGCTACGGTTCCGTCATCCGCGGCCGGCCGAAAAGTGGACCGGCGTG |
| 181-240 | CTGAACACGACCACACCGCCCAACAGCTGCGTGCAGATCGTGGACACCGTGTTCGGCGAC |
| 241-300 | TTCCCGGGCGCGACCATGTGGAACCCGAACACGCCCCTGTCCGAGGACTGTCTGTACATT |
| 301-360 | AACGTGGTGGCACCGCGACCCCGGCCCAAGAATGCGGCCGTCATGCTGTGGATCTTCGGC |
| 361-420 | GGCGGCTTCTACTCCGGCACCGCCACCCTGGACGTGTACGACCACCGGGCGCTTGCGTCG |
| 421-480 | GAGGAGAACGTGATCGTGGTGTCGCTGCAGTACCGCGTGGCCAGTCTGGGCTTCCTGTTT |
| 481-540 | CTCGGCACCCCGGAAGCGCCGGGCAATGCGGGACTGTTCGATCAGAACCTTGCGCTACGC |
| 541-600 | TGGGTGCGGGACAACATTCACCGGTTCGGTGGCGATCCGTCGCGTGTGACACTGTTCGGC |
| 601-660 | GAGAGTGCCGGTGCCGTCTCGGTGTCGCTGCATCTGCTGTCCGCCCTTTCCCGCGATCTGT |
| 661-720 | TCCAGCGGGCCATCCTGCAGAGCGGCTCGCCGACGGCACCGTGGGCATTGGTATCGCGCG |
| 721-780 | AGGAAGCCACACTAAGAGCACTGCGGTTGGCCGAGGCGGTCGGCTGCCCGCACGAACCGA |
| 881-840 | GCAAGCTGAGCGATGCGGTCGAGTGCCTGCGCGGCAAGGACCCGCACGTGCTGGTCAACA |
| 1041-900 | ACGAGTGGGGCACGCTCGGCATTTGCGAGTTCCCGTTCGTGCCGGTGGTCGACGGTGCGT |
| 1101-960 | TCCTGGACGAGACGCCGCAGCGTTCGCTCGCCAGCGGGCGCTTCAAGAAGACGGAGATCC |
| 1161-1020 | TCACCGGCAGCAACACGGAGGAGGGCTACTACTTCATCATCTACTACCTGACCGAGCTGC |
| 1021-1080 | TGCGCAAGGAGGAGGGCGTGACCGTGACGCGCGAGGAGTTCCTGCAGGCGGTGCGCGAG |
| 1081-1140 | CTCAACCCGTACGTGAACGGGGCGGCCCGGCAGGCGATCGTGTTCGAGTACACCGACTGG |
| 1141-1200 | ACCGAGCCGGACAACCCGAACAGCAACCGGGACGCGCTGGACAAGATGGTGGGCGACTAT |
| 1201-1260 | CACTTCACCTGCAACGTGAACGAGTTCGCGCAGCGGTACGCCGAGGAGGGCAACAACGTC |
| 1261-1320 | TACATGTATCTGTACACGCACCGCAGCAAAGGCAACCCGTGGCCGCGCTGGACGGGCGTG |
| 1321-1380 | ATGCACGGCGACGAGATCAACTACGTGTTCGGCGAACCGCTCAACCCCACCCTCGGCTACA |
| 1381-1440 | CCGAGGACGAGAAAGACTTTAGCCGGAAGATCATGCGATACTGGTCCAACTTTGCCAAAA |
| 1441-1500 | CCGGCAATCCAAATCCCAACACGGCCAGCAGCGAATTCCCCGAGTGGCCCAAGCACACCG |
| 1501-1560 | CCCACGGACGGCACTATCTGGAGCTGGGCCTCAACACGTCCTTCGTCGGTCGGGGCCCACG |
| 1561-1620 | GTTGAGGCAGTGTGCCTTCTGGAAGAAGTACCTTCCCCAGCTAGTTGCAGCTACCTCGAAC |
| 1621-1639 | CTACCAGGGTAG |

FIG. 2

SEQUENCE LISTING

<160> NUMBER OF SEQ ID NOS: 1

<210> SEQ ID NO 1
<211> LENGTH: 1635
<212> TYPE: DNA
<213> ORGANISM: Anopheles gambiae
<220> FEATURE:
<221> NAME/KEY: gene
<222> LOCATION: (162)..(702)

<400> SEQUENCE: 1
gacgcgaacg acaacgatcc gctggtggtc aacacggata aggggcgcat ccgcggcatt 60
acggtcgatg cgcccagcgg caagaaggtg gacgtgtggc tcggcattcc ctacgcccag 120
ccgccggtcg ggccgctacg gttccgtcat ccgcggccgg ccgaaaagtg gaccggcgtg 180
ctgaacacga ccacaccgcc caacagctgc gtgcagatcg tggacaccgt gttcggcgac 240
ttcccgggcg cgaccatgtg gaacccgaac acgcccctgt ccgaggactg tctgtacatt 300
aacgtggtgg caccgcgacc ccggcccaag aatgcggccg tcatgctgtg gatcttcggc 360
ggcggcttct actccggcac cgccaccctg gacgtgtacg accaccgggc gcttgcgtcg 420
gaggagaacg tgatcgtggt gtcgctgcag taccgcgtgg ccagtctggg cttcctgttt 480
ctcggcaccc cggaagcgcc gggcaatgcg ggactgttcg atcagaacct tgcgctacgc 540
tgggtgcggg acaacattca ccggttcggt ggcgatccgt cgcgtgtgac actgttcggc 600
gagagtgccg gtgccgtctc ggtgtcgctg catctgctgt ccgccctttc ccgcgatctg 660
ttccagcggg ccatcctgca gagcggctcg ccgacggcac cgtgggcatt ggtatcgcgc 720
gaggaagcca cactaagagc actgcggttg gccgaggcgg tcggctgccc gcacgaaccg 780
agcaagctga gcgatgcggt cgagtgcctg cgcggcaagg acccgcacgt gctggtcaac 840
aacgagtggg gcacgctcgg catttgcgag ttcccgttcg tgccggtggt cgacggtgcg 900
ttcctggacg agacgccgca gcgttcgctc gccagcgggc gcttcaagaa gacggagatc 960
ctcaccggca gcaacacgga ggagggctac tacttcatca tctactacct gaccgagctg 1020
ctgcgcaagg aggagggcgt gaccgtgacg cgcgaggagt tcctgcaggc ggtgcgcgag 1080
ctcaacccgt acgtgaacgg ggcggcccgg caggcgatcg tgttcgagta caccgactgg 1140
accgagccgg acaacccgaa cagcaaccgg gacgcgctgg acaagatggt gggcgactat 1200
cacttcacct gcaacgtgaa cgagttcgcg cagcggtacg ccgaggaggg caacaacgtc 1260

-continued

```
tacatgtatc tgtacacgca ccgcagcaaa ggcaacccgt ggccgcgctg gacgggcgtg   1320

atgcacggcg acgagatcaa ctacgtgttc ggcgaaccgc tcaaccccac cctcggctac   1380

accgaggacg agaaagactt tagccggaag atcatgcgat actggtccaa ctttgccaaa   1440

accggcaatc caaatcccaa cacggccagc agcgaattcc ccgagtggcc caagcacacc   1500

gcccacggac ggcactatct ggagctgggc ctcaacacgt ccttcgtcgg tcggggccca   1560

cggttgaggc agtgtgcctt ctggaagaag taccttcccc agctagttgc agctacctcg   1620

aacctaccag ggtag                                                    1635
```

SYSTEM AND METHOD FOR CREATING CRYSTALS OF INSECT ACETYLCHOLINESTERASE

RELATED APPLICATIONS

This application claims the benefit of U.S. Provisional Patent Application No. 62/524,728, filed Jun. 26, 2017.

BACKGROUND OF THE INVENTION

1. Field of the Invention

In general, the present invention relates to the creation of crystals from acetylcholinesterase and to systems that utilize such crystals to produce digital models through X-ray crystallography. More particularly, the present invention relates to the methodology of creating crystals from insect acetylcholinesterase.

2. Prior Art Description

Acetylcholinesterase, also known as AChE is a serine protease that hydrolyzes the neurotransmitter acetylcholine (Ach). AChE is found at mainly neuromuscular junctions and cholinergic brain synapses, where it serves to terminate synaptic transmission. For a cholinergic neuron to receive another impulse, ACh must be released from the ACh receptor. This occurs only when the concentration of ACh in the synaptic cleft is very low.

During neurotransmission, ACh is released from the nerve into the synaptic cleft and binds to ACh receptors on the post-synaptic membrane, therein relaying the signal from the nerve. AChE, which is also located on the post-synaptic membrane, terminates the signal transmission by hydrolyzing the ACh, therein liberating a choline. The liberated choline is taken up again by the pre-synaptic nerve and ACh is synthesized by combining with acetyl-CoA through the action of choline acetyltransferase.

Inhibition of AChE leads to accumulation of ACh in the synaptic cleft. This results in impeded neurotransmission or a cessation of neurotransmission. Consequently, inhibition of AChE may lead to death. As a result, inhibitors of AChE have proven to be very effective nerve toxins and insecticides. Therefore, by studying compounds that inhibit AChE in various insects, a pathway for studying insecticides may be found that is useful in the targeted control of pest insects, such as the species of mosquito that carries malaria.

In use, the residual spraying of anticholinesterase insecticides has been useful in controlling insects, such as the mosquitos that spread malaria. However, widespread application of anticholinesterase insecticides has led to mutations and the rise of insecticide-resistant insect strains. In mosquitos, common insecticide-resistant mosquito strains include a G280S mutation, which is sometimes referred to as a G119S mutation. This mutation affects enzyme acetylcholinesterase in the insect nervous system, therein inhibiting the effects of the insecticide.

To the best of the Applicant's knowledge, there are no structures of mosquito AgAChE that are available that include the G280S mutation and that are useful for X-ray crystallography. In the prior art, the Applicant has previously developed a system and method of obtaining high-resolution crystal structures of human AChE. Such a system and method are disclosed in co-pending U.S. patent application Ser. No. 15/469,227. However, the application to mutated insect AChE remain undisclosed.

In order to effectively study the effects of any compound that reacts with insect AChE, the insect AChE must first be accurately modeled. The way that insect AChE is modeled requires that crystals of insect AChE be formed. The crystals are then subjected to X-ray crystallography. X-ray crystallography is a method used for determining the atomic and molecular structure of a crystal, in which the crystalline atoms cause a beam of X-rays to diffract into many specific directions. By measuring the angles and intensities of these diffracted beams, a crystallographer can produce a three-dimensional model of the density of electrons within the crystal. From this study of electron density, the mean positions of the atoms in the crystal can be determined, as well as their chemical bonds, their disorder, and various other information that can be used to create an accurate digital model.

A need therefore exists for a system and method of creating better crystals of insect AChE, therein resulting in better modeling using X-ray crystallography. This need is met by the present invention as described below.

SUMMARY OF THE INVENTION

The present invention is a method of creating crystals of insect acetylcholinesterase, such as mosquito acetylcholinesterase. The method includes obtaining a first polynucleotide that encodes for acetylcholinesterase in a targeted insect. The first polynucleotide contains a targeted catalytic core sequence that is required for biological functioning and is constant across different cDNA sources for the insect species. The targeted catalytic core sequence has a known sequence of bases between a specific first codon and a stop codon.

A recombinant DNA construct is formed by adding a fusion protein and a polyhistidine tag to the targeted catalytic core sequence prior to the specified first codon. The recombinant DNA construct is amplified. Additionally, the recombinant DNA construct can be further modified by adding known mutations that cause resistance to acetylcholinesterase inhibitor insecticides.

Bacterial cell colonies on a growth medium are transfected with the recombinant DNA construct. The cell colonies package the DNA construct into a larger DNA construct that can be isolated. This larger DNA construct which contains the recombinant DNA can be used to produce a virus in insect cells which causes them to secrete a polypeptide encoded by contained recombinant DNA construct into the growth medium. The polypeptide includes the polyhistidine tag and part of the targeted catalytic core sequence between the polyhistidine tag and the stop codon.

The polypeptide encoded by the recombinant DNA construct is separated from the growth medium to form a concentrate. The polyhistidine tag is removed from the concentrate. The concentrate is exchanged into a buffer to create a buffered concentrate. Crystals, suitable for X-ray crystallography are then grown with the buffered concentrate.

BRIEF DESCRIPTION OF THE DRAWINGS

For a better understanding of the present invention, reference is made to the following description of an exemplary embodiment thereof, considered in conjunction with the accompanying drawings, in which:

FIG. 2 is a table showing the full polynucleotide represented by FIG. 1;

DETAILED DESCRIPTION OF THE DRAWINGS

The present invention methodology can be used to model insect acetylcholinesterase (AChE). The methodology is especially adapted for modeling insect AChE that contains mutations that make the insect resistant to AChE inhibitor insecticides. Although the methodology can be used to model AChE for a variety of insects, such as agricultural pests, the present invention methodology is particularly useful in modeling disease carrying insects, such as mosquitos. Accordingly, in describing the present invention methodology, its application to mosquito AChE is used as the exemplary embodiment. Mosquitos have known genetic mutations that make some mosquitos resistant to insecticides and therefore provide one of the best examples for describing the methodology. The methodology described and illustrated is exemplary and can be varied using undescribed, yet functionally equivalent process steps. The methodology described, however, is merely exemplary and should not be considered a limitation to the novelty of the invention as described.

Figure 1:
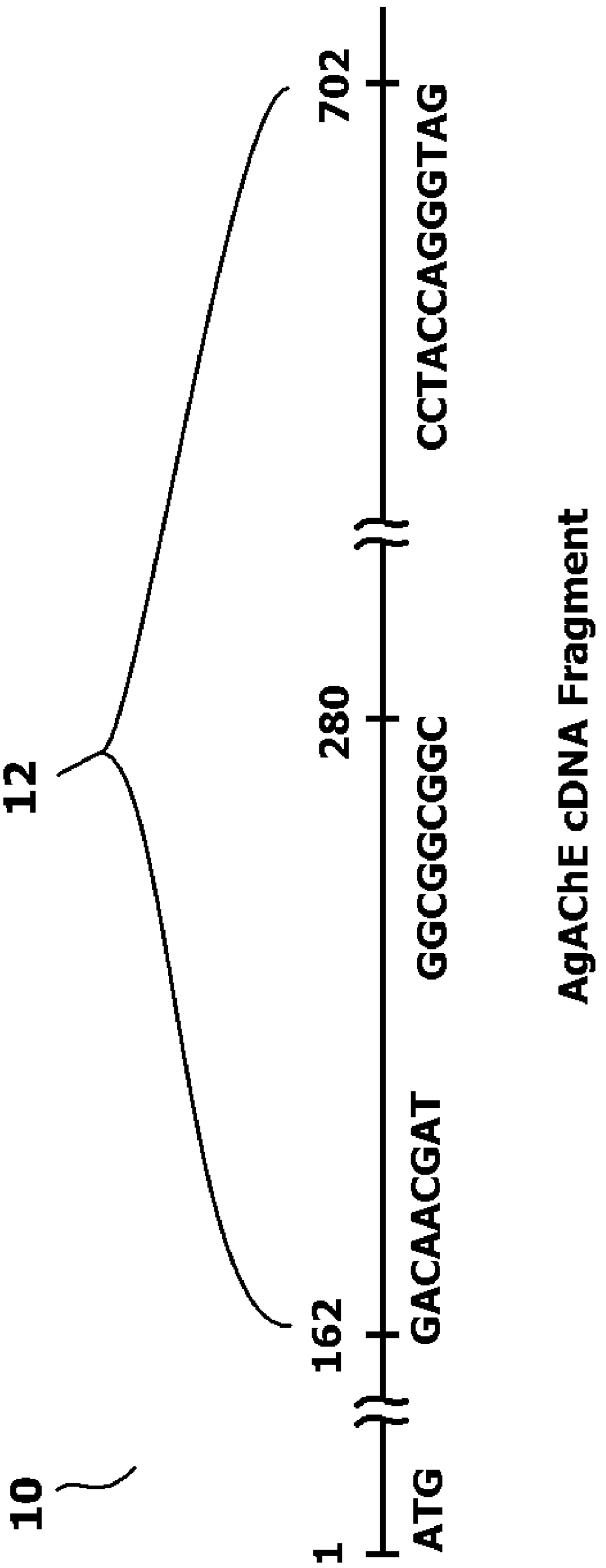
FIG. 1 shows a representation of a polynucleotide that encodes for mosquito AChE, part 12 is codon 162 to codon 702 of SEQ ID NO: 1.

Referring to FIG. 1, it can be seen that the process begins with obtaining a cloned DNA (cDNA) fragment 10 for a targeted insect. In the current example, the targeted insect is the mosquito (*Anopheles gambiae*) that is commonly known to carry malaria. The cDNA fragment 10 contains a gene sequence (ACE-1 gene) that codes for acetylcholinesterase of the mosquito. The cDNA fragment 10 is identified as SEQ ID No. 1, the DNA sequence of which has been separately filed. The cDNA 10 is also presented in the polynucleotide sequence table shown in FIG. 2, wherein the polynucleotide sequence in SEQ ID No. 1 and the polynucleotide sequence shown in the table of FIG. 2 are the same. The ACE-1 gene cDNA fragment 10 is obtained from a commercial source. The ACE-1 gene cDNA fragment 10 contains multiple bases in its sequence. The depicted ACE-1 gene cDNA fragment 10 contains the entire open reading frame of base sequences that codes for AChE in the malaria mosquito (*Anopheles gambiae*), starting at initiating codon 1 (ATG) and ending at stop codon 709 (TAG). A targeted catalytic core sequence 12 found to be critical to the biological function of AChE is contained within the open reading frame beginning at codon 162 (GAC) and ending at codon 702 (GGG). It will therefore be understood that the targeted catalytic core sequence 12 is a sequence of 540 codons. The targeted catalytic core sequence 12 encodes for selective aspects of selected mosquito AChE (AgAChE), wherein each sequential three-base combination is a codon that encodes for an amino acid in the AgAChE protein. Although different clone cell stocks for AgAChE may exist, the targeted catalytic core sequence 12 is the same across sources for the same species of mosquito.

Figure 3:
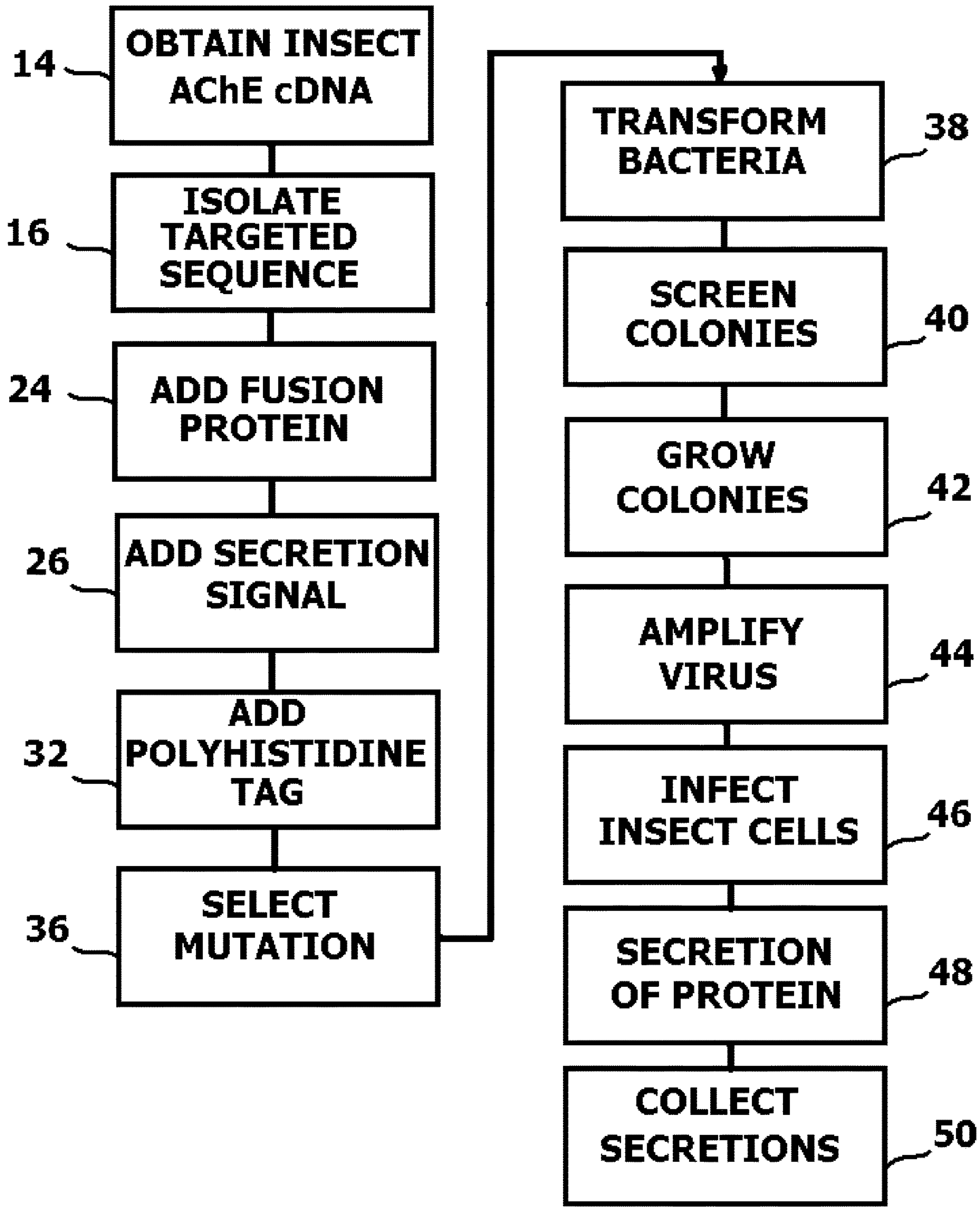
FIG. 3 is a block logic-flow diagram that illustrates a first part of the present invention methodology.
Figure 4:
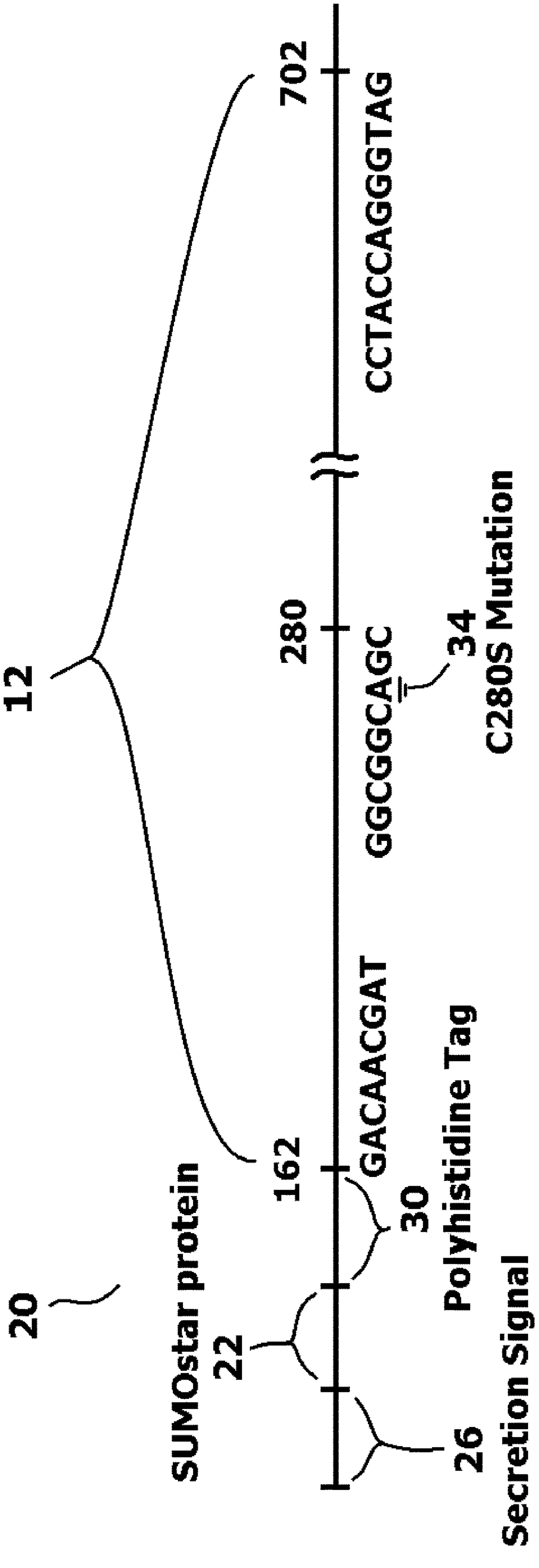
FIG. 4 shows a representation of a recombinant DNA construct created, in part, from the polynucleotide of FIG. 1, part 12 is codon 162 to codon 702 of SEQ ID NO: 1.

Referring to FIG. 3 and FIG. 4 in conjunction with FIG. 1, it can be seen that the ACE-1 gene cDNA fragment 10 is obtained from a commercial source. See Block 14. The targeted catalytic core sequence 12 of the reading frame codon sequence is then isolated using conventional molecular biology techniques. See Block 16. Steps are then taken to convert the targeted catalytic core sequence 12 into the recombinant construct 20 illustrated in FIG. 3.

To create the recombinant DNA construct 20, the targeted catalytic core sequence 12 that has been isolated is altered. A DNA coding sequences for a yeast SUMOstar fusion protein 22 is fused to the front end of the targeted catalytic core sequence 12. This is accomplished using molecular biology techniques, such as overlap extension polymerase chain reaction (PCR) protocols to enhance protein expression and secretion of complex proteins. This corresponds to a position prior to codon 162 of the initial ACE-1 gene cDNA fragment 10. See Block 24. The recombinant fusion also provides a secretion signal 26 that later directs the secretion of produced proteins into a cell growth media. See Block 28.

A TEV-protease cleavable polyhistidine tag 30 is added to the recombinant DNA construct 20. See Block 32. The TEV-protease cleavable polyhistidine tag 32 is inserted between the yeast SUMOstar fusion protein 22 and the first codon of the targeted catalytic core sequence 12 at codon 162 (GAC) of the initial ACE-1 gene cDNA fragment 10. See FIG. 4.

One or more selected mutations can be added to the recombinant DNA construct 20. In the illustrated example, a G280S mutation 34 is inserted into the targeted catalytic core sequence 12 after codon 280 of the initial ACE-1 gene cDNA fragment 10. The mutation is added using a commercial baculovirus expression system, such as the Invitrogen™ Bac-to-Bac™ brand baculovirus expression system sold by Life Technology Corporation. The baculovirus expression system contains a baculovirus shuttle vector. A selected mutation is introduced into the baculovirus shuttle vector that produces a specific mutation, such as a G280S insecticide-resistant mutation. See Block 36. It will be understood that the illustrated introduction of a G280S insecticide-resistant mutation is exemplary. Other known mutations that effect insecticide resistance can also be used. The bacterial strain for the selected mutation is transformed with the baculovirus shuttle vector and colonies are screened for recombination events which cause the bacteria to produce baculovirus DNA (bacmid). See Block 38. The baculovirus DNA is screened and colonies grow. See Block 40 and Block 42.

A growth medium of insect cells is prepared and transfected with the baculovirus DNA. An initial virus is produced and used to infect larger cultures of insect cells. This amplifies the virus. See Block 44. A final culture of insect cells in a cell growth medium are infected by the amplified virus. See Block 46. Due to the secretion signal 26 and SUMOstar fusion protein 22 present in the recombinant DNA construct 20, the recombinant AgAChE G280S mutant fusion protein is secreted into the cell growth medium for harvesting. See Block 48. After secretion, the cells are removed and what is left is the remnants of the cell growth medium that contains the secreted recombinant AChE G280S fusion protein. That is, the cell colonies secrete the segment of the recombinant DNA construct 20 that corresponds from the polyhistidine tag 30 before base position 162 to stop codon TAG just beyond base position 574. The secreted recombinant AChE G280S fusion protein is still tagged with the polyhistidine tag 30. The remnants of the cell growth medium contacting the secreted recombinant AgAChE G280S fusion protein is collected. See Block 50.

Figure 5:
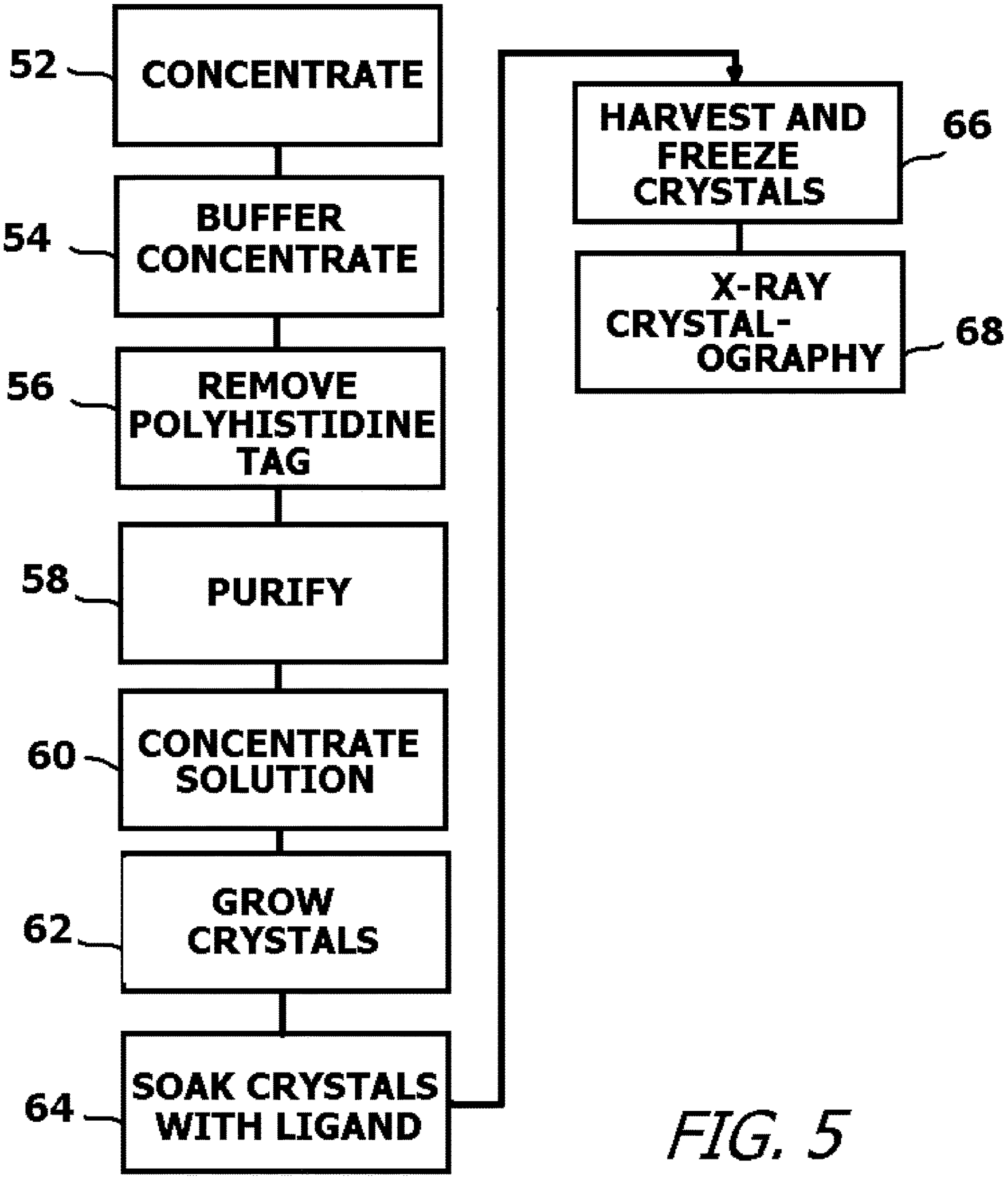
FIG. 5 is a block logic-flow diagram that illustrates a second part of the present invention methodology.

Referring to FIG. 5, in conjunction with FIG. 4, the process is continued. The tagged recombinant AgAChE G280S fusion protein is separated from the remnants of the cell growth medium. The tagged recombinant AgAChE G280S fusion protein that is removed is then concentrated. See Block 52. A binding buffer is provided. A preferred binding buffer contains 20 mM 4-(2-hydroxyethyl)piperazine-1-ethanesulfonic acid (HEPES) pH 7.6, 500 mM NaCl, and 40 mM imidazole. The tagged recombinant AgAChE concentrate is then exchanged into the binding buffer using cross-flow diafiltration cells. See Block 54. After purification, the polyhistidine tag 30 is cleaved from the tagged recombinant AgAChE G280S fusion protein, using a his-TEV protease. This leaves the desired cleaved protein. See Block 56. The cleaved AgAChE G280S protein is then purified by being passed over a 1 mL Ni-NTA agarose gravity column to remove the his-TEV protease, any cleaved tag residues, and any residual un-cleaved proteins. This produces a purified AgAChE G280S protein. See Block 58.

The purified AgAChE G280S protein is dialyzed overnight into a storage buffer, such as 10 mM HEPES (pH 7.0) and 10 mM NaCl. The solution is concentrated to 5 mg/ml for crystallization. See Block 60.

Crystals of the purified AgAChE G280S protein are grown by sitting drop vapor diffusion at 4° C. against the crystallization buffer. See Block 62. Hexagonal rod-shaped crystals (20 μm×20 μm×300 μm) are typically nucleated within 14 days and grow to full size over 60 days. Once the crystals are full size, they are harvested. The crystals can be used directly, but are preferably soaked in a ligand, prior to harvesting. See Block 64. Alternatively, a ligand can be mixed with the crystallization buffer. The harvested crystals can then be cut and subjected to X-ray crystallography and modeling in the traditional manner. See Block 66 and Block 68.

It will be understood that the method steps of the present invention that are illustrated and described are merely exemplary and that a person skilled in the art can make many variations to those method steps. All such embodiments are intended to be included within the scope of the present invention as defined by the appended claims.

What is claimed is:

1. A method of creating crystals of mosquito acetylcholinesterase, comprising the steps of:

isolating a first polynucleotide encoding mosquito acetylcholinesterase, wherein said first polynucleotide encodes a targeted catalytic core sequence required for biological functioning, wherein said targeted catalytic core sequence extends from a first codon to a stop codon;

forming a recombinant DNA construct by combining a polynucleotide sequence encoding a SUMOstar fusion partner and a polyhistidine tag with said targeted catalytic core polynucleotide sequence prior to said first codon;

amplifying said recombinant DNA construct;

transfecting cells on a growth medium with said recombinant DNA construct to create a colony of cells, wherein said colony of cells secrete a recombinant fusion partner-polyhistidine-mosquito acetylcholinesterase polypeptide into said growth medium;

separating said recombinant fusion partner-polyhistidine-mosquito acetylcholinesterase polypeptide from said growth medium to form a concentrate;

cleaving said fusion partner-polyhistidine tag from the mosquito acetylcholinesterase polypeptide and removing said fusion partner-polyhistidine tag from said concentrate;

exchanging said concentrate into a buffer to create a buffered concentrate; and growing crystals of the recombinant mosquito acetylcholinesterase with said buffered concentrate.

2. The method according to claim 1, further including adding a mutation to the polynucleotide encoding said targeted catalytic core sequence.

3. The method according to claim 2, wherein said mutation results in a mosquito acetylcholinesterase polypeptide resistant to an acetylcholinesterase inhibitor insecticide.

4. The method according to claim 2, wherein adding a mutation to said polynucleotide encoding the targeted catalytic core is performed by employing baculovirus to produce baculovirus DNA.

5. The method according to claim 4, wherein adding a mutation to said polynucleotide encoding the targeted catalytic core further includes providing a growth medium of insect cells and transfecting said insect cells with said baculovirus DNA to produce an amplified virus.

6. The method according to claim 5, wherein adding a mutation to said polynucleotide encoding the targeted catalytic core further includes transfecting said recombinant DNA construct with said amplified virus.

7. The method according to claim 1, wherein said polynucleotide encoding the SUMOstar protein is added to said polynucleotide encoding the targeted catalytic core with polymerase chain reaction protocols.

8. The method according to claim 2, wherein said mosquito acetylcholinesterase is from the genus *Anopheles gambiae* and said mutation is at a codon that results in a G280S amino acid mutation, wherein the amino acid numbering corresponds to wild-type *Anopheles gambiae* acetylcholinesterase.

9. The method according to claim 1, wherein said first codon of said targeted catalytic core is GAC.

10. The method according to claim 1, wherein said targeted catalytic core has 540 bases between said first codon and said stop codon.

11. The method according to claim 1, wherein growing crystals with said buffered concentrate includes using sitting drop vapor diffusion with a crystallization buffer.

12. The method according to claim 11, further including the step of mixing a ligand into said buffered concentrate.

13. The method according to claim 1, further including the step of dipping said crystals in a solution containing a ligand.

14. A method of creating crystals of mosquito acetylcholinesterase, comprising the steps of:

isolating a first polynucleotide that encodes for mosquito acetylcholinesterase from the genus *Anopheles gambiae*, wherein said first polynucleotide begins with base sequence GACAAC which includes GAC as the first codon;

attaching a polynucleotide encoding a polyhistidine tag to said first polynucleotide prior to said first codon GAC;

attaching a polynucleotide encoding a SUMOstar protein to said first polynucleotide, wherein said polynucleotide encoding the polyhistidine tag is interposed between said polynucleotide encoding the SUMOstar protein and said first codon GAC, therein producing a recombinant DNA construct;

transfecting cells on a growth medium with said recombinant DNA construct to create a colony of cells, wherein said colony of cells secretes a recombinant SUMOstar-polyhistidine-mosquito acetylcholinesterase polypeptide into said growth medium;

separating said recombinant SUMOstar-polyhistidine-mosquito acetylcholinesterase polypeptide from said growth medium to form a concentrate;

cleaving said SUMOstar-polyhistidine tag from the mosquito acetylcholinesterase polypeptide and removing said SUMOstar-polyhistidine tag from said concentrate;

exchanging said concentrate into a buffer to create a buffered concentrate; and growing crystals of a mosquito acetylcholinesterase polypeptide with said buffered concentrate.

15. The method according to claim 14, further including the step of introducing a mutation to the polynucleotide encoding the mosquito acetylcholinesterase polypeptide.

16. The method according to claim 15, wherein said mutation is introduced by infecting said colony of cells with an engineered virus.

* * * * *